US006577141B2

(12) United States Patent
Gandrud

(10) Patent No.: US 6,577,141 B2
(45) Date of Patent: Jun. 10, 2003

(54) SYSTEM AND METHOD FOR CAPACITANCE SENSING OF PAVEMENT DENSITY

(75) Inventor: Michael D. Gandrud, Ames, IA (US)

(73) Assignee: Sauer-Danfoss, Inc., Ames, IA (US)

( * ) Notice: Subject to any disclaimer, the term of this patent is extended or adjusted under 35 U.S.C. 154(b) by 65 days.

(21) Appl. No.: 09/880,400

(22) Filed: Jun. 13, 2001

(65) Prior Publication Data

US 2002/0190728 A1 Dec. 19, 2002

(51) Int. Cl.[7] .............................................. G01R 27/26
(52) U.S. Cl. ...................................................... 324/663
(58) Field of Search ................................ 324/644, 663, 324/675, 687, 698; 702/33, 137; 73/32 R; 340/562, 601, 603, 612

(56) References Cited

U.S. PATENT DOCUMENTS

| 3,784,905 A | * | 1/1974 | Blackwell ..................... 324/61 |
| 5,900,736 A | * | 5/1999 | Sovik et al. ................. 324/663 |
| 5,952,561 A |   | 9/1999 | Jaselskis et al. ............... 73/78 |
| 6,122,601 A | * | 9/2000 | Swanson et al. ............ 702/137 |
| 6,400,161 B1 | * | 6/2002 | Geisel ........................ 324/644 |
| 6,401,068 B1 | * | 6/2002 | Cherveny et al. ........... 704/275 |

OTHER PUBLICATIONS

Capacitive Proximity Sensors Manual—"Non–contact detection of non–metallic materials"—Balluff.
"Capacitive Proximity Sensors and Solutions" Stedham Electronics Corporation.

* cited by examiner

Primary Examiner—Safet Metjahic
Assistant Examiner—Etienne P LeRoux

(57) ABSTRACT

The present invention discloses a system and method of determining the density of pavement material. The invention includes positioning a capacitive proximity sensor, adjacent to but not in direct contact with a pavement material, projecting an electrostatic capacitive field from the sensor in the direction of the pavement material, measuring the strength of the electrostatic capacitive field as detected by the sensor, and correlating the strength of the electrostatic capacitive field to the density of the pavement material. The invention further discloses determining a location and associating the location with a pavement material density.

19 Claims, 3 Drawing Sheets

SYSTEM AND METHOD FOR CAPACITANCE SENSING OF PAVEMENT DENSITY

BACKGROUND OF THE INVENTION

This invention relates to non-destructive sensing of pavement density. More specifically, the invention relates to use of capacitive proximity sensing to determine pavement material density.

In paving, asphalt pavement is often used. In the asphalt paving process, various grades of aggregate are used. The aggregate is mixed with asphalt cement (tar). There are also air voids within the mix. A hot asphalt mix as laid has more air voids than is desirable. A paver lays down the asphalt mix and levels the asphalt mix with a series of augers and scrapers. The material as laid is not dense enough due to the number of air voids in the asphalt mix. Therefore, a roller makes a number of passes over the layer of asphalt material (mat), driving back and forth, or otherwise creating sufficient compaction to form asphalt of the strength needed for the road surface.

There are a number of problems associated with this process of paving. These problems relate to determining when there is sufficient compaction of the asphalt. If the asphalt is not sufficiently compacted, the quality of the pavement suffers. The amount of compaction is dependent upon a number of factors including the asphalt cement content, the aggregate type, the aggregate size, the aggregate shape, the aggregate texture, the distribution gradation, filler content, the mix temperature, the speed of the roller, the number of passes of the roller, irregularities in the roller performance, and other factors.

It is important for the asphalt mat to be of proper density. If there is not proper density, there will be long term deterioration when the asphalt begins to crack or there may be other problems related to stability and durability.

The density of the asphalt mat is increased through repeated compression with the roller. Preferably, the asphalt is uniformly dense throughout. There are numerous problems associated with determining the density of the asphalt so that one can be assured of the resulting stability of the asphalt mat.

One method of determining density is through use of a nuclear gage. In this process, a number of different measurements are taken from different locations on the asphalt mat. Nuclear density measurement systems suffer from any of the following; high cost, safety issues of radioactive materials, need to drive a probe or spike into the mat; thereby leaving a hole in the mat, inability to measure density on a continuous basis, unfeasibility of installing a plurality of such machines on a piece of road construction equipment.

Other approaches have also been used to measure density. One such approach is a Capacitance Energy Dissipation (CED) method. The CED approach involves using a capacitor charged to a voltage to energize a plate in contact with the asphalt. Direct current then flows from the capacitor into the ground as the capacitor discharges. The time required to discharge the capacitor is measured and this time is compared to the discharge rate of a reference capacitor with a known discharge rate. There are also a number of problems associated with this method. One problem is that this method is dependent upon temperature. Another problem is that the capacitor plate must come in contact with the pavement, so that the contact plate would need to be periodically cleaned. Another problem is that there is a time associated with the discharge rate that may impede the ability to continuously measure pavement density.

Therefore there are a number of problems associated with measuring pavement density. Thus, it is a primary object of the present invention to provide an improved system and method for measuring pavement density.

Another object of the present invention is to provide a system and method for measuring pavement density that does not require a sensor to come into contact with the pavement.

Another object of the present invention is to provide a system and method for measuring pavement density that provides for non-destructive evaluation.

Yet another object of the present invention is to provide a system and method for measuring pavement density that is more sensitive to density of the top portion of the mat.

A further object of the present invention is to provide a system and method for measuring pavement density that reduces cost and complexity.

Another object of the present invention is to provide a system and method for measuring relative pavement density.

These and other objects of the present invention will become apparent from the following description.

BRIEF SUMMARY OF THE INVENTION

The invention is a system and method for capacitive sensing of pavement material density. One or more capacitive proximity sensors are positioned adjacent to but not in contact with a pavement material such as an asphalt mat. The measurements from the sensors are correlated to known particular asphalt densities. Based on these test density readings, it is known whether further compaction is required.

DETAILED DESCRIPTION OF THE INVENTION

Figure 1:
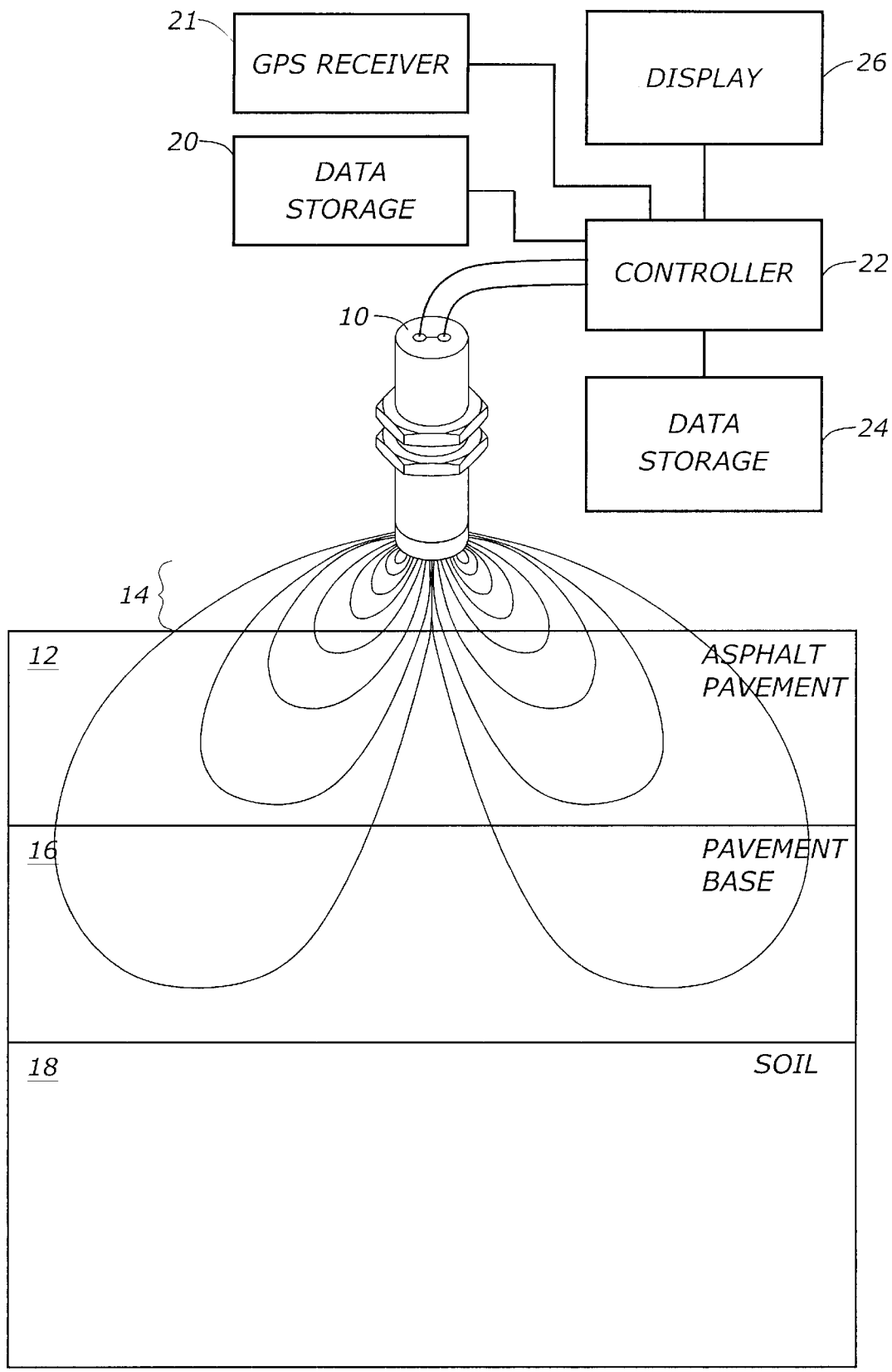
FIG. 1 is a diagram of the pavement density sensing system of the present invention.

FIG. 1 is a diagram showing an overview of the capacitive proximity sensing system. In FIG. 1, there is a capacitive proximity sensor 10. The capacitive proximity sensor 10 may be a BCAW-030-NB-1-Y-3 or other capacitive proximity sensor. This sensor has an analog output, the magnitude of the analog output is a function of the sensed electrostatic capacitive field that is generated by the capacitive proximity sensor. The present invention contemplates that other capacitive proximity sensors providing output signals, whether current or voltage, may be used. The present invention also contemplates that the output may be digital provided sufficient resolution is available. The capacitive proximity sensor used is of a dielectric type as opposed to a capacitor of the conductive type. The capacitive proximity sensor is positioned above the pavement material such as an asphalt mat 12. A distance 14 separates capacitive proximity sensor 10 and asphalt mat 12. The capacitive proximity sensor 10 generates an electrostatic capacitive field. The presence of the asphalt mat 12 in proximity to the capacitive proximity sensor 10 changes the measurement of the electrostatic capacitive field as measured by capacitive proximity sensor 10. The electrostatic capacitive field sensed is related to the distance 14 as well as the dielectric constant of the material being sensed.

The distance between the capacitive proximity sensor 10 and the asphalt mat 12 should be a fixed or known distance. Tests have indicated that a distance of approximately one centimeter is effective. However, the present invention contemplates that a range of distances may work, for example just above contact such as approximately one-half millimeters to a distance of ten or more centimeters. The material being sensed is that which comes within the operative limits of the capacitive proximity sensor and typically is the asphalt pavement 12 and potentially the material under the asphalt pavement 12, such as the pavement base 16 and the soil 18. The capacitive proximity sensor 10 is more sensitive to the top most portion of the asphalt mat. For strength and stability purposes, it is most important that the top most portion be of proper density.

The present invention contemplates that the capacitive proximity sensor 10 is capable of being adjusted for sensitivity. Adjustment may involve altering the distance between the sensor and the asphalt mat or making adjustments to the sensor itself by adjustments built into the sensor or by electronic circuitry. The capacitive proximity sensor 10 is electrically connected to a controller 22. The controller 22 is a microprocessor, a micro controller, a computer, a digital signal processor, a circuit, a processor, an integrated circuit, a portion of an integrated circuit, or other control. The controller 22 receives the sensed electrostatic capacitive field measurement. The present invention contemplates that signal conditioning and/or analog to digital conversion may need to be performed, depending on the particular controls selected and the particular capacitive proximity sensors selected. Once data is received, the controller can perform numerous operations. For example, the controller 22 can store the data to a memory or data storage unit 24. The data storage unit 24 can be any of a number of types of storage including EPROM, EEPROM, flash memory, magnetic memory, optical memory, and other memory or storage devices. The data stored may later be compared or correlated with data calculated or measured in other ways, such as through core samples. This allows one to calibrate the capacitive proximity sensor 10 accordingly if required or made desirable by different distances 14, different moisture content, different thicknesses of asphalt pavement, different mixtures of asphalt, or other reason.

The controller 22 is optionally attached to network interface 20. The network interface 20 allows the controller 22 to communicate over a network. For example, the network can be a Controller Area Network (CAN). The present invention however contemplates that any number of networks may be used in order to communicate information pertaining to pavement capacitance, density, or other measurements or diagnostic information from the controller to another device and/or location. In addition, the present invention contemplates that a location determination device such as a GPS receiver 21 is operatively connected to the controller 22. In this manner, the controller 22 can receive location information and associate that information with measurements and/or calculated information.

In addition, the controller 22 is operatively connected to the display 26. The controller 22 may correlate the capacitance measured by sensor 10 to a pavement density. The capacitance over the pavement density is displayed on the display 26. The present invention contemplates that the density calculated, stored, and/or displayed may be a relative density.

Figure 2:
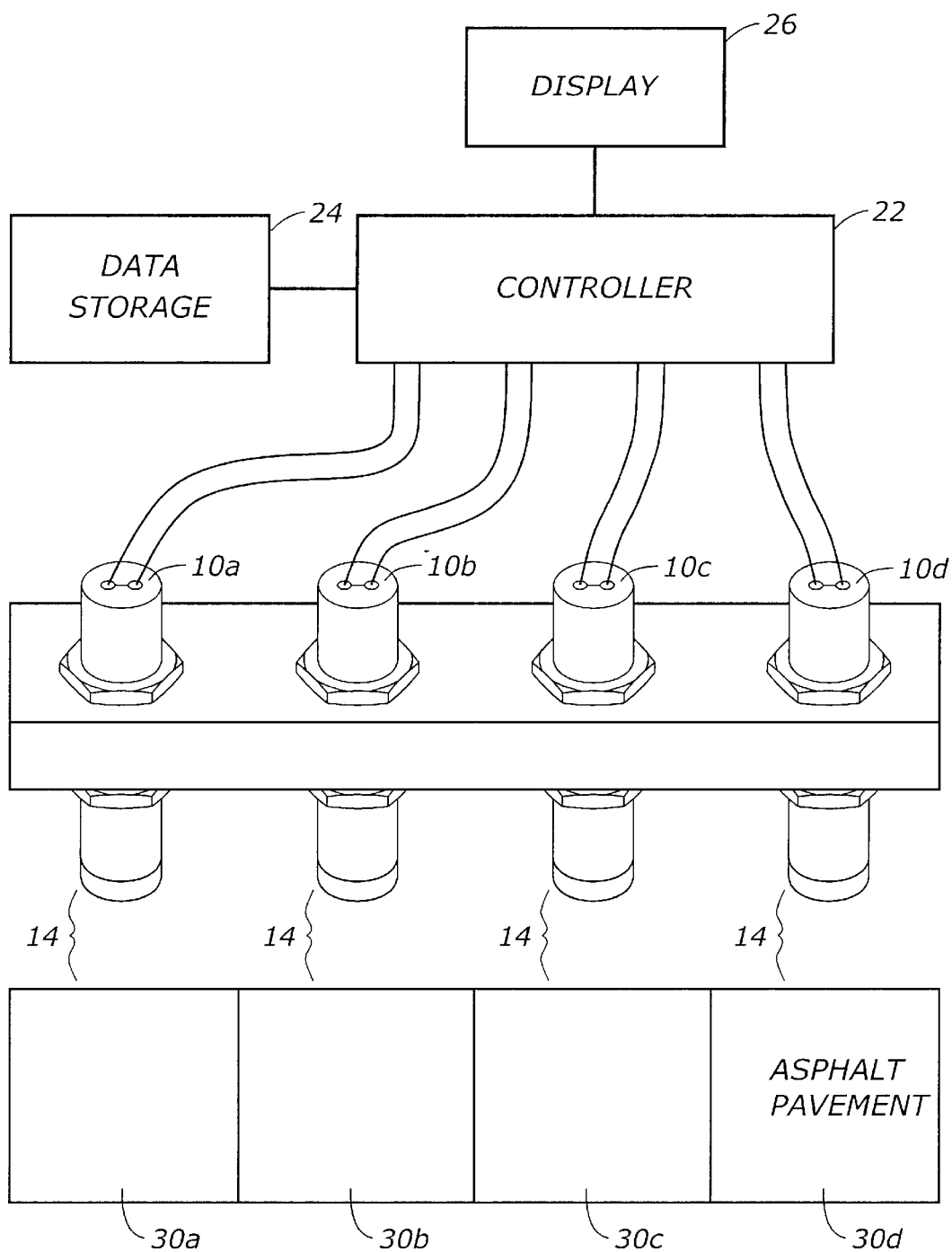
FIG. 2 is a diagram of a capacitive sensing system with multiple sensors.

FIG. 2 shows the system of the present invention with multiple capacitive proximity sensors 10. The capacitive proximity sensors 10 are mounted on a support structure such as a bar 28. The controller 22 is connected to all of the capacitive proximity sensors. This permits the controller 22 to receive sensor data from each sensor and each portion of asphalt pavement associated with each sensor. The controller 22 calculates a relative pavement density. For example, the controller 22 compares the data from each of the sensors to determine the pavement portion with the lowest density. Similarly, the controller 22 determines the asphalt pavement portion with the highest density. If the multiple capacitive proximity sensor readings are relatively close, then the controller determines that the density is uniform. By comparing the measured density of each strip of pavement with the desired density, the controller determines if additional compaction of the asphalt pavement is required for a particular portion of the asphalt pavement.

The controller 22 can also correlate the capacitance directly to a density. Then the controller calculates the densities associated with each portion of the asphalt pavement and displays these densities on the display 26. The controller 22 then compares these calculated densities to a threshold density. The threshold density can be a minimal density or a maximum density and can be a range of densities. For example, the threshold density may be any density within a set defined by as those densities between a minimum density and a maximum density. The threshold density is a known density or relative density. For example, the threshold may be defined as a density determined experimentally. There is a capacitance associated with the density which is the threshold capacitance. The precise density need not be numerically calculated, instead the capacitance of a sufficiently dense pavement sample is used to set the threshold density. Thus, in this manner, the capacitance is correlated to a density. Alternatively, densities are calculated. The present invention contemplates that measured capacitances are correlated to relative densities or to actual densities that are mathematically calculated for a particular capacitance or are estimated, looked up in an experimentally defined table or otherwise defined. If the calculated densities are less than the threshold density then the controller causes the display 26 to display a message that further compaction is required.

When multiple sensors are used, each sensor is associated with a particular portion or strip of asphalt pavement. Preferably, the capacitive sensors simultaneously sense the capacitance associated with the respective strips of asphalt pavement.

The display includes a bar graph display with a bar associated with each strip of asphalt pavement. Based upon the bar graph display, an operator determines which strips of pavement require additional compaction.

The present invention contemplates that the support structure 28 is located on, or is a part of a roller. Thus, as the pavement is being compacted by the roller, the density of the pavement is monitored to determine whether additional passes need to be made over the asphalt material to compact it or to determine whether additional passes need to be made only over certain portions of the asphalt pavement material. In addition, this density data is stored in data storage 24 to provide documentation that the pavement is of sufficient density to comply with construction standards.

The present invention contemplates that one or more capacitive pavement density sensors can be installed on a roller or other machine. A location receiver, such as a Global Positioning System (GPS), GLOSNASS or other navigational receiver or similar device can be installed on the machine to determine machine position. The machine position is then recorded while measuring pavement density therefore creating a record of final pavement density associated with particular locations. The road surface is then broken into a grid with each element or cell of the grid having a dimension of 20 cm. The present invention is not limited to a particular type of navigational receiver or to a particular size of grid. The present invention contemplates numerous variations such as may be convenient or appropriate given a particular set of circumstances. The record of the pavement density and location is used to document if a strip of pavement fell between roller passes and was not rolled or was not sufficiently rolled. This system allows and enables documentation of the quality of the pavement of every grid location.

Figure 3:
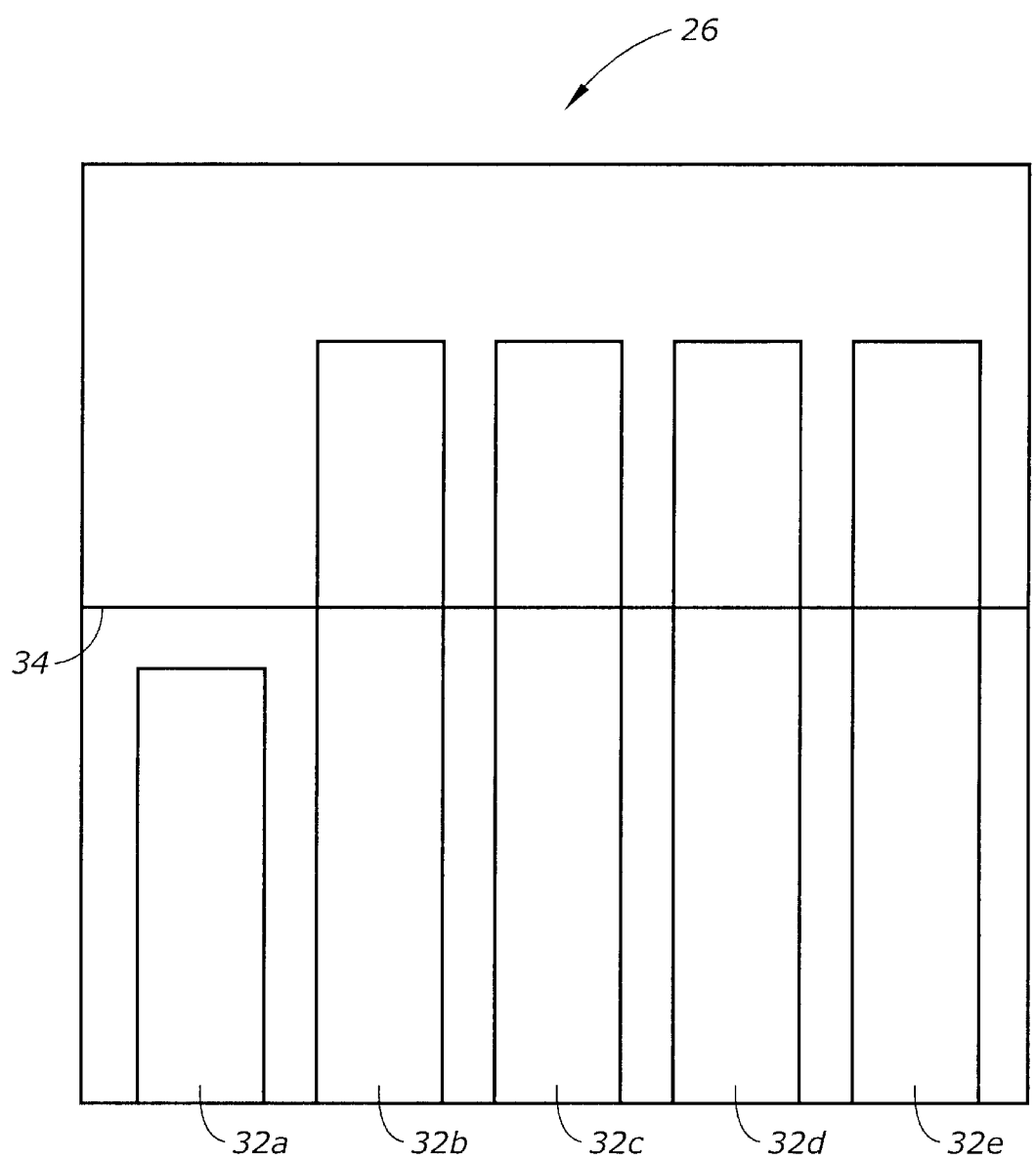
FIG. 3 is a diagram of a display of the present invention.

FIG. 3 shows a diagrammatic representation of a display 26 of the present invention. Display 26 includes multiple bars 32 associated with capacitive proximity sensors. For example, FIG. 2 shows capacitive proximity sensor 10A that detects and measures the electrostatic capacitive field associated with asphalt pavement strip 30A. FIG. 3 shows bar 32A, which is a relative density of asphalt pavement strip 30A. Similarly, in FIG. 3 densities associated with other strips of asphalt pavement are shown. In addition, a line 34 is set according to a required pavement density, a standard associated with a required pavement density or other threshold. Thus, a roller operator is apprised as to which portion of the asphalt pavement requires additional compaction. If bar 32A falls below required pavement density line 34, the asphalt pavement strip associated with bar 32A requires additional compaction.

Thus, a method and system of pavement density sensing has been disclosed. The present invention contemplates numerous variations in the particular capacity proximity sensors being used, the distance between capacity proximity sensors and asphalt pavement, the controller used, the display used, the data storage used, and other variations.

What is claimed is:

1. A method of determining density of pavement material comprising:

positioning a capacitive proximity sensor adjacent to but not in direct contact with a pavement material;

projecting an electrostatic capacitive field from the sensor in the direction of the pavement material; measuring the strength of the electrostatic capacitive field as detected by the sensor; and correlating the strength of the electrostatic capacitive field to the density of the pavement material.

2. The method of claim 1 further comprising adjusting the sensitivity of the capacitive proximity sensor.

3. The method of claim 1 further comprising adjusting the measured electrostatic capacitive field for moisture content of the pavement material.

4. The method of claim 1 further comprising recording the measured strength of the electrostatic capacitive field as detected by the capacitive proximity sensor.

5. The method of claim 1 wherein the step of correlating is comparing the measured changes associated with the sample pavement material with measured changes associated with a second sample of pavement material, the density of the sample relative to the density of the second sample being known.

6. The method of claim 1 further comprising determining a location of the capacitive proximity sensor and associating that location with a pavement density as determined by said sensor.

7. The method of claim 6 further comprising storing the location and the associated pavement density.

8. A system for measuring pavement material density comprising:

at least one capacitive proximity sensor capable of simultaneously projecting an electrostatic capacitive field and detecting and measuring the strength of that electrostatic capacitive field from a location remote from the pavement material;

a controller cooperatively connected to the capacitive proximity sensor wherein the controller receives the measured strength of the electrostatic capacitive field and correlates the measured strength to a pavement material density.

9. The system of claim 8 further comprising a display, the display operatively connected to the controller, the controller sending a signal to the display, the signal related to pavement density.

10. The system of claim 8 further comprising a data storage component, the data storage component operatively connected to the controller, the controller sending data to the data storage component.

11. The system of claim 10 wherein the data is capacitive proximity sensor measurements.

12. The system of claim 10 wherein the data is pavement material density.

13. The system of claim 8 wherein the pavement material density is a density relative to a known sample standard density.

14. The system of claim 8 further comprising a location determination device, the location determination device operatively connected to the controller.

15. The system of claim 14 wherein the location determination device is a GPS receiver.

16. The system of claim 14 further comprising a memory operatively connected to the controller adapted to store pavement material density data and corresponding location data.

17. The system of claim 14 further comprising a display operatively connected to the controller adapted to display pavement material density data and corresponding location data.

18. The system of claim 8 further comprising a network interface operatively connected to the controller.

19. The system of claim 18 wherein the network interface is a controller area network interface.

* * * * *